(12) United States Patent
Hashimoto et al.

(10) Patent No.: US 9,732,010 B2
(45) Date of Patent: Aug. 15, 2017

(54) CATALYST FOR METHANATION OF CARBON OXIDES, PREPARATION METHOD OF THE CATALYST AND PROCESS FOR THE METHANATION

(71) Applicants: HITACHI ZOSEN CORPORATION, Osaka-shi, Osaka (JP); Koji Hashimoto, Miyagi-ken (JP)

(72) Inventors: Koji Hashimoto, Miyagi-ken (JP); Hiroyuki Takano, Osaka (JP); Kouichi Izumiya, Osaka (JP); Naokazu Kumagai, Osaka (JP); Zenta Kato, Miyagi-ken (JP); Hiroyuki Shinomiya, Miyagi-ken (JP)

(73) Assignees: HITACHI ZOSEN CORPORATION, Osaka-shi (JP); Koji Hashimoto, Miyagi-ken (JP)

( * ) Notice: Subject to any disclaimer, the term of this patent is extended or adjusted under 35 U.S.C. 154(b) by 0 days.

(21) Appl. No.: 15/443,241

(22) Filed: Feb. 27, 2017

(65) Prior Publication Data
US 2017/0166492 A1    Jun. 15, 2017

Related U.S. Application Data

(62) Division of application No. 12/184,493, filed on Aug. 1, 2008, now Pat. No. 9,617,196.

(30) Foreign Application Priority Data

Aug. 3, 2007  (JP) ................................. 2007-203653
Jul. 18, 2008  (JP) ................................. 2008-187970

(51) Int. Cl.
*B01J 21/00*    (2006.01)
*B01J 23/00*    (2006.01)
(Continued)

(52) U.S. Cl.
CPC ................. *C07C 1/12* (2013.01); *B01J 23/78* (2013.01); *B01J 23/83* (2013.01); *C07C 2523/78* (2013.01); *C07C 2523/83* (2013.01)

(58) Field of Classification Search
USPC .................................. 502/100, 300, 305, 308
See application file for complete search history.

(56) References Cited

U.S. PATENT DOCUMENTS

| 3,988,263 A | 10/1976 | Hansford |
| 5,786,294 A * | 7/1998 | Sachtler ................. B01J 37/033 502/217 |

(Continued)

FOREIGN PATENT DOCUMENTS

| EP | 0004456 A1 | 10/1979 |
| EP | 0216472 A1 | 4/1987 |

(Continued)

OTHER PUBLICATIONS

Habazaki et al., Methanation of Carbon Dioxide on Catalysts Derived from Amroophous Ni—Zr-Rare Earth Alloys, Studies in Surface Science and Catalysis, vol. 114, 261-266, (Jan. 1, 1998).

(Continued)

*Primary Examiner* — James McDonough
(74) *Attorney, Agent, or Firm* — Kratz, Quintos & Hanson, LLP

(57) ABSTRACT

Disclosed is a catalyst for methanation reaction producing methane with high conversion by reaction of hydrogen with carbon dioxide, or a gas mixture of carbon dioxide and carbon monoxide, or a gas mixture containing these compounds as the main components. The catalyst is prepared by the steps of mixing (A) aqueous zirconia sol with salts of (B) stabilizing element(s), which is selected from the group consisting of Y, La, Ce, Pr, Nd, Sm, Gd, Dy, Ca and Mg, and (C) iron group element(s), drying and calcining the mixture to obtain a catalyst precursor, and subsequent reduction of (Continued)

the precursor. The catalyst comprises, by atomic %, A: 18-70%, B: 1-20% and C: 25-80% based on the elemental states of the metals. The catalyst is characterized by multiple oxide of tetragonal zirconia structure, in which not only the stabilizing element(s) but also a part of the iron group element(s) is incorporated, and on which the iron group element(s) in the metallic state is supported.

3 Claims, 1 Drawing Sheet

(51) Int. Cl.
  *B01J 25/00* (2006.01)
  *B01J 29/00* (2006.01)
  *C07C 1/12* (2006.01)
  *B01J 23/83* (2006.01)
  *B01J 23/78* (2006.01)

(56) References Cited

U.S. PATENT DOCUMENTS

| | | | |
|---|---|---|---|
| 6,034,029 A * | 3/2000 | Wulff-Doring | B01J 21/066 423/544 |
| 6,326,329 B1 * | 12/2001 | Nunan | B01D 53/945 502/242 |
| 2008/0299028 A1 * | 12/2008 | Slaten | B01D 53/8628 423/351 |

FOREIGN PATENT DOCUMENTS

| | | |
|---|---|---|
| GB | 2291819 A | 2/1996 |
| JP | S62-034986 A | 2/1987 |
| JP | S63-024979 A | 5/1988 |
| JP | 07-076528 A | 3/1995 |
| JP | 08-127545 A | 5/1996 |
| JP | 10-043594 A | 2/1998 |
| JP | 10-244158 A | 9/1998 |
| JP | 10-263400 A | 10/1998 |
| JP | 11-090227 A | 4/1999 |
| JP | 2000-126596 A | 5/2000 |
| JP | 2000-254508 A | 9/2000 |
| JP | 2007-076528 A | 3/2007 |
| JP | 2007-252990 A | 10/2007 |
| JP | 2008-127545 A | 6/2008 |
| JP | 2008-155147 A | 7/2008 |
| JP | 2010-043594 A | 2/2010 |
| JP | 2010-520807 A | 6/2010 |
| JP | 2010-244158 A | 10/2010 |
| JP | 2010-263400 A | 11/2010 |
| JP | 2011-090227 A | 5/2011 |
| WO | 2007/025691 A1 | 3/2007 |
| WO | 2008/110331 A1 | 9/2008 |

OTHER PUBLICATIONS

Habazaki et al., Co-Methanation of Carbon Monoxide and Carbon Dioxide on Supported Nickel and Cobalt Catalysts Prepared from Amorphous Alloys, Applied Catalyst A: General, Elsevier Science, Amsterdam, vol. 172, No. 1, 131-140 (Aug. 24, 1998).

Jun et al., Structure and Catalytic Properties of Ceria-Based Nickel Catalyst for CO2 Reforming of Methane, Catalysis Surveys from Asia, vol. 11, No. 3, 97-113, (Jul. 25, 2007).

Li et al., Preparation of Ni/YSZ Materials for SOFC Anodes by Buffer-Solution Method, Materials Science and Engineering, Elsevier Sequoia Lausanne, CH, vol. 86, No. 2, 119-122 (Sep. 25, 2001).

Razpotnik et al., Preparation of NiO/YSZ Powders Using a Pechini-Type Method, Materiali in Tehnologije-Materials and Technology, Institute Za Kovinske Mateirale, Ljubljana, S1, vol. 40, No. 2, 69-72, (Jan. 1, 2006).

Roh et al., Carbon Dioxide Reforming of Methane over Ni Incorporated into Ce—ZrO2 Catalysts, Applied Catalysis A: General, Elsevier Science, Amsterdam, vol. 276, No. 1-2, 231-239 (Nov. 25, 2004).

Yamasaki et al., Compositional Dependence of the CO2 Methanation Activity of Ni/ZrO2 Catalysts Prepared from Amorphous Ni—Zr Alloy Precursors, Applied Catalysis A: General, 163, 187-197 (1997).

Yamasaki et al., Characterization of CO2 Methanation Catalysts Prepared from Amorphous Ni—Zr and Ni—Zr-rare earth element Alloys, Studies in Surface Science and Catalysis, vol. 114, 451-454 (Jan. 1, 1998).

Yamasaki et al., Creation of Methanation Catalyst for Carbon Dioxide Utilizing Amorphous Ni—Zr-RE Alloy as Precursor, Materials and Environment, vol. 44, 73-76 (1997).

Yamasaki et al., Effect of Tetragonal ZrO2 on the Catalytic Activity of Ni/ZrO2 Catalyst Prepared from Amorphous Ni—Zr Alloys, Catalysis Communications, Elsevier Science, Amsterdam, vol. 7, No. 1, 24-28, (Aug. 1, 2006).

* cited by examiner

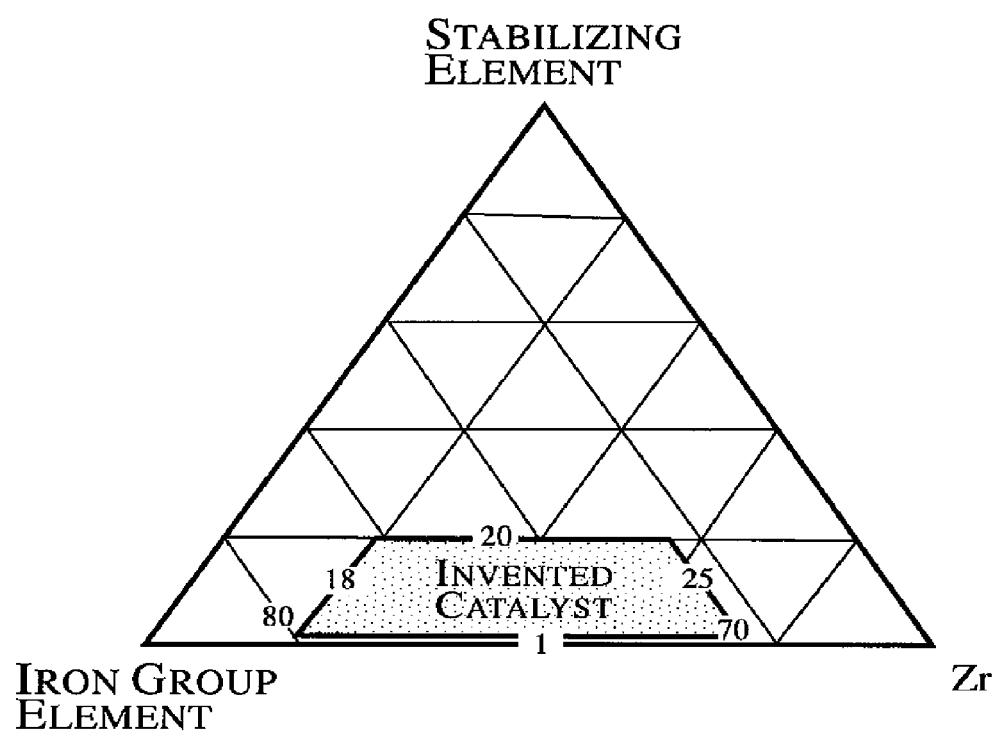

CATALYST FOR METHANATION OF CARBON OXIDES, PREPARATION METHOD OF THE CATALYST AND PROCESS FOR THE METHANATION

CROSS REFERENCE TO RELATED APPLICATIONS

This application is a divisional application of U.S. patent application Ser. No. 12/184,493, filed Aug. 1, 2008, which claims priority to Japanese Patent Application No. 2007-203653, filed Aug. 3, 2007, and Japanese Patent Application No. 2008-187970, filed Jul. 18, 2008, which are hereby incorporated herein by reference in their entirety.

BACKGROUND OF THE INVENTION

Field in the Industry

The present invention concerns a catalyst for methanation or formation of methane by reaction of hydrogen with carbon dioxide, a mixture of carbon monoxide and dioxide, or a mixed gas containing them as the main components. The invention also concerns method of preparing the catalyst and the process for the methanation using the catalyst.

STATE OF THE ART

Global warming due to carbon emissions as a result of combustion of fossil fuels is getting serious, and ways for decreasing the emission have been sought. As one of the countermeasures, the method of producing methane by reaction of carbon dioxide with hydrogen is expected to prevent global warming and supply fuel. Also, hope is placed on the technology of producing fuel gas with high combustion energy by methanation from low combustion energy gas mixture of hydrogen, carbon monoxide and carbon dioxide formed by gasification of coke, coal, biomass, activated sludge, and so on.

To date Raney nickel and catalysts supported on alumina or silica have been examined as the catalysts for methane production by contact reaction of hydrogen with carbon dioxide, carbon monoxide or their mixture. However, because reaction rates with these catalysts are so slow that the reaction should be carried out under a high pressure.

The inventors discovered the fact that ribbon-shaped amorphous alloys, prepared by rapid quenching of the liquid state, consisting of an iron group element such as Ni and Co, and a valve metal such as Zr, Ti, Nb and Ta are effective catalysts for methane synthesis, and disclosed as Japanese Patent Disclosure Nos. 10-43594, 10-244158 and 10-263400. The selectivity to methane formation achieved by these catalysts is almost 100% and the conversion rate is very fast at ambient pressure. However, the process for producing the catalyst alloys, rapid quenching from the liquid state, is not suitable for mass production, and the applicable systems of ribbon-shaped catalysts are limited.

On the basis of the above-mentioned discovery the inventors developed a method of producing powder-shaped catalyst, mass-production of which is much easier than the ribbon-shaped catalysts, and disclosed as Japanese Patent Disclosure No. 2000-254508. This catalyst is composed of Ni supported on tetragonal $ZrO_2$, and prepared by calcination of tetragonal zirconia-type oxides including tetragonal structure-stabilizing elements (Y, La, Ce, Pr, Nd, Sm, Gd, Tb, Dy, Eu, Mg and/or Ca), followed by impregnation of Ni and/or Co and final reduction to form metallic Ni and/or Co.

The catalyst disclosed in Japanese Patent Disclosure No. 2000-254508 includes the following embodiments:

(1) A catalyst for carbon dioxide methanation, which comprises Ni and/or Co supported on tetragonal zirconia-type supporter containing a stabilizing element or elements selected from the group consisting of Y, La, Ce, Pr, Nd, Sm, Gd, Tb, Dy, Eu, Mg and/or Ca, wherein the ratio of Zr to the sum of Zr and the stabilizing element(s) is 85 atomic % or more and wherein the ratio of Ni and/or Co to the total metallic elements is 0.05-0.5.

(2) The method of preparing the catalyst for carbon dioxide methanation, which comprising the steps of forming tetragonal zirconia-type supporter by addition of one or more of salts selected from the group consisting of Y, La, Ce, Pr, Nd, Sm, Gd, Tb, Dy, Eu, Mg and Ca to aqueous zirconia sol under stirring, drying and calcining, and immersing the tetragonal zirconia-type supporter in a solution of a salt or salts of Ni and Co, drying calcining, and final reduction.

As the result of further research the inventors discovered the fact that, instead of impregnation of Ni and/or Co to tetragonal zirconia-type oxide previously prepared as described in Japanese Patent Disclosure No. 2000-254508, preparation of oxide containing all the components necessary for the catalyst and subsequent reduction will give a catalyst with better performance, and thus, achieved the new invention.

SUMMARY OF THE INVENTION

The object of the present invention is to provide a catalyst for carbon dioxide methanation with high activity and selectivity even at a temperature of 250° C. or lower, which is useful also for production of methane by the reaction of the gas mixture of carbon dioxide, carbon monoxide and hydrogen utilizing the above-noted novel method of producing the catalyst.

The catalyst according to the present invention is the catalyst for methanation reaction by hydrogenation of carbon dioxide, mixture of carbon dioxide and carbon monoxide, mixed gas containing these gases as the main component, which comprises, the total being 100% based on the metals in the elemental states:

A) a tetragonal zirconia structure-stabilizing element, one or more selected from the group consisting Y, La, Sm, Ce, Pr, Nd, Gd, Dy, Ca and Mg: 1-20 atomic %;
B) Zr for composing tetragonal zirconia supporter: 18-70 atomic %; and
C) an iron group element bearing the catalytic activity: 25-80 atomic %;
and in the catalyst the iron group element is supported on the oxide of the tetragonal zirconia structure in which not only the stabilizing element but also a portion of the iron group element is incorporated to stabilize the tetragonal zirconia structure.

BRIEF EXPLANATION OF THE DRAWING

The attached single drawing is a diagram showing chemical composition of the catalyst according to the invention.

DETAILED EXPLANATION OF THE PREFERRED EMBODIMENTS

The method of preparing the catalyst according to the present invention is the method of preparing the above-described catalyst for the methanation reaction, which comprises the steps of mixing hydrosol of zirconia, aqueous solution of salts of the stabilizing element(s) and the iron group element(s) in the ratio satisfying the above-noted conditions for the catalyst composition, and subsequent reducing treatment so as to realize the catalyst structure of supporting the iron group element on the oxide of the tetragonal zirconia structure in which not only the stabilizing element but also a portion of the iron group element is incorporated in the crystal structure.

The method of preparing the catalyst according to the present invention is characterized by employing, not the two step method as disclosed in Japanese Patent Disclosure No. 2000-254508 comprising formation of the supporter with tetragonal zirconia structure and impregnating aqueous solution of the salt of the active metal followed by reduction, but the one step method by mixing all the necessary components in the form of aqueous solutions, drying and calcinations followed by reduction.

According to the above-described one step method, in the process of drying to calcinations, mixture of iron group element oxide and multiple oxide containing not only the stabilizing element(s) but also the iron group element(s) is formed. The oxide of the iron group element is reduced during the subsequent reduction, and as the result, the catalyst having the structure where the iron group element of the metallic state is supported on the multiple oxide of tetragonal zirconia structure is formed. In this manner after the reduction a portion of iron group element(s) remains in the supporter, which is multiple oxide of tetragonal zirconia structure, in addition to the stabilizing element(s).

It is possible to form catalyst grains of maximum 3 mm diameter by mixing the mixture of zirconia hydrosol, a salt of the stabilizing element and a salt of the iron group element with silica, alumina or other oxide particles as the core of the catalyst and a binder such as silicate, titanate, aluminate and zirconate, and subsequent drying and calcination. The core particles and the binders may be used in an alternative way such as mixing core particles and a binder with already prepared catalyst powder followed by calcination.

The catalyst according to the present invention is explained in detail. The stabilizing elements, Y, La, Ce, Pr, Nd, Sm, Gd, Dy, Ca and Mg are the constituents to stabilize the tetragonal zirconia structure during crystallization of zirconia from sol. Thus, the stabilizing element(s) is necessary in an amount of 1 atomic % or more, but excess addition is harmful to the catalyst activity due to formation of its own oxide. The addition of the stabilizing elements should be at highest 20 atomic %.

Zr is the essential element to form the supporter of tetragonal zirconia structure, and it is necessary to add 18 atomic % or more. However, if too large amount is added, concentration of the iron group element(s) will not be so high as sufficient to the catalyst activity, and hence, 70 atomic % is set as the maximum content.

The iron group element is the catalytically, active component, and 25 atomic % or more is necessary to exist in the catalyst. However, excess addition of the element leads to coagulation causing lowered dispersion with consequent decrease in the activity. Thus, addition of the element should be 80 atomic % or less. As the iron group element Ni must necessarily be used. Apart of Ni can be replaced with the other iron group element(s), Fe and/or Co. In that case, the atomic ratio of Ni to the sum of iron group elements must be 0.6 or higher.

High activity and durability of the catalyst according to the invention can be explained as follows. The stable phase of zirconium oxide is monoclinic. However, the active component, the iron group element supported on the tetragonal zirconia which is stabilized by inclusion of stabilizing element(s) exhibits particularly high activity for methanation of carbon dioxide and carbon monoxide. This has been explained in Japanese Patent Disclosure No. 2000-254508.

The present invention is the fruits of further development, which utilizes the facts that calcination of mixture of aqueous zirconia sol, solutions of the salts of stabilizing element(s) and the iron group element(s) causes formation of mixture of oxide(s) of the iron group element(s) and multiple oxide of tetragonal zirconia structure consisting of oxidized zirconium, and stabilizing element(s), in which a part of the oxidized iron group element(s) is incorporated, and that, when the mixture of oxides is subjected to hydrogen treatment, the multiple oxide containing zirconium and the stabilizing element(s) with high affinity to oxygen remains in the oxidized state and only the oxide of the iron group element(s) directly contacted to hydrogen is reduced to the metallic state. Thus, the catalyst in which catalytically active iron group element(s) in the metallic state is finely dispersed on the multiple oxide of tetragonal zirconia structure is obtained.

In such the catalyst, even if the metallic iron group element(s) on the catalyst surface is lost by abrasion due to passage of reaction gases, the iron group element(s) in the oxidized state emerges from the inner parts and is readily reduced by hydrogen in the reaction gases, and thus, acts as the active substance. Hence, the state of high activity of the catalyst due to finely dispersed active sites on the tetragonal zirconia can be preserved.

Procedures for preparing the catalyst according to the present invention are as follows: one or more salts of the stabilizing element(s) selected from the group consisting of Y, La, Ce, Pr, Nd, Sm, Gd, Dy, Ca and Mg is mixed with aqueous zirconia sol, and to the mixture, an aqueous solution of Ni salt, or Ni salt with Fe salt and/or Co salt is added. The resulting mixture is concentrated by heating under stirring to dry, and calcined at about 500° C. in air to form mixture of the multiple oxide of the tetragonal zirconia structure and the oxide(s) of the iron group element(s). Reduction treatment of the mixture of the oxides in hydrogen stream at about 300° C. gives the catalyst in which the metallic iron group element(s) is supported on the multiple oxide of tetragonal zirconia structure.

Table 1 shows composition of the catalyst of the present invention.

TABLE 1

| | | Elements composing tetragonal zirconia supporter | Elements acting as active site in catalysis |
|---|---|---|---|
| Composition | Zr | Y, La, Ce, Pr, Nd, Sm, Gd, Dy, Ca, Mg | Iron group element: Ni or Ni with Fe and/or Co (The ratio of Ni to the sum of iron group elements must be 0.6 or higher) |
| Content | 18-70 atomic % | 1-20 atomic % | 25-80 atomic % |

The catalyst according to the present invention in which metallic state iron group element(s), Ni or Ni with Fe and/or Co is supported on the multiple oxide of tetragonal zirconia structure exhibits methane selectivity of neary 100%, and the reaction equilibrium is extremely product-sided even under a normal pressure. Thus, problem of complicated procedures of repeating the reaction under high pressures after removal of impurities from the reaction mixture to recycle the unreacted materials is solved. Now, complicated system and equipment for circulation of reactants is no longer necessary, and conversion of a gas mixture of hydrogen with carbon dioxide, carbon monoxide or their mixture to methane is rapidly performed under ambient pressure instead of high pressures.

On the catalyst of the present invention an ideal situation can be realized: poisonous carbon monoxide in the gas mixture of carbon monoxide, carbon dioxide and hydrogen is preferentially and selectively converted to methane, and thereafter, carbon dioxide is converted to methane with the remaining hydrogen. Furthermore, the production of the catalyst according to the present invention is easy.

During the methanation of carbon monoxide, the iron group element in the oxidized state, particularly, nickel contained in the tetragonal zirconia lattice may be sometimes selectively lost by the reaction with carbon monoxide. However, even if oxidized nickel is lost, the tetragonal zirconia structure remains as stabilized by the presence of the stabilizing element(s), and hence, the high catalytic activity is retained without being changed.

EXAMPLES

Example 1

To 15.0 g of aqueous zirconia sol "Zr30AH" (Nissan Chemical) (30 wt. % Zr, pH 4.0), 1.58 g of $Sm(NO_3)_3 \cdot 6H_2O$ was added, and stirring was carried out until creamy sludge was formed. A nickel nitrate solution was prepared by dissolving 19.806 g of $Ni(NO_3)_2 \cdot 6H_2O$ in 20 ml of water. The nickel nitrate solution was mixed with the zirconia sol-samarium nitrate sludge under stirring. After standing still for 1 hour, the mixture was kept in a muffle furnace at 150° C. for 4 hours to remove water and dry. Then, the dry substance was calcined by heating at 500° C. for 8 hours to obtain calcined black solid, the weight of which was 10.3 g. The black solid was pulverized in an agate mortar and the resulting powder was classified with a sieve of 100 mesh to give the catalyst precursor. The metallic fraction of Ni in the catalyst precursor was 0.625 and the composition was written as $Ni_{0.625}(Zr_{0.692}Sm_{0.108}O_{1.946})_{0.375}$. The tetragonal polymorph of zirconia was identified by X-ray diffraction with Cu-Kα radiation. The specific area of the precursor was 80.1 $m^2/g$.

A quartz tube of inner diameter 15 mm was used as a reactor, and 5.0 g of the above-obtained catalyst precursor was inserted on quartz wool in the quartz tube. The catalyst precursor in the reactor was reduced by heating at 300° C. in an electric furnace under hydrogen stream for 2 hours. The catalyst was thus obtained.

A gas mixture, in which the volume ratio of carbon dioxide to hydrogen was 1/4, was passed through the reactor containing the catalyst at 250° C. After the reaction the gas was passed through a cold water trap to remove water and then analyzed by gas chromatography. The analysis of methane and unreacted carbon dioxide and hydrogen revealed that the conversion of carbon dioxide on 1 g of the oxide mixture of the catalyst precursor at the gas flow rate of 5.4 L/h was 82.2%, and that the reaction product was only methane showing the 100% methane selectivity.

Control Example

Carbon dioxide conversion of the catalyst having the composition of $Ni_{0.5}(Zr_{0.833}Sm_{0.167}O_{1.92})_{0.5}$, i.e., metallic fraction of Ni in the catalyst being 0.5, which was one of the catalysts described in Japanese Patent Disclosure No. 2000-254508, was reported to be 52.6% on 1 g of the Ni-impregnated catalyst precursor at the gas flow rate of 4 L/hour at 250° C.

Example 2

Catalysts were prepared by the same procedures as Example 1 using various compositions of Ni, stabilizing element(s) and Zr. Carbon dioxide conversion was examined in regard to the respective catalysts by the same procedures as those of Example 1. The results are shown in Table 2. All the catalysts showed high conversion at 200° C. and 250° C., indicating the excellent performance of the catalysts.

TABLE 2

| | Composition of the Metal Elements Atomic % | | | $CO_2$ Conversion % | |
|---|---|---|---|---|---|
| No. | Ni | Zr | Stabilizing Element | 200° C. | 250° C. |
| 2 | 25 | 62.5 | Y 12.5 | 39.2 | 59.6 |
| 3 | 50 | 41.7 | Y 8.3 | 45.5 | 68.9 |
| 4 | 70 | 25 | Y 5 | 38.1 | 56.1 |
| 5 | 25 | 62.5 | La 12.5 | 42.1 | 67.1 |
| 6 | 57 | 33 | La 10 | 59.5 | 73.2 |
| 7 | 25 | 62.5 | Ce 12.5 | 40.1 | 66.7 |
| 8 | 50 | 41.7 | Ce 8.3 | 50.6 | 69.7 |
| 9 | 25 | 63 | Pr 12 | 49.8 | 66.3 |
| 10 | 57 | 33 | Pr 10 | 58.7 | 72.5 |
| 11 | 25 | 63 | Nd 12 | 50.2 | 67.1 |
| 12 | 57 | 33 | Nd 10 | 60.1 | 73.2 |
| 13 | 25 | 56.3 | Sm 18.7 | 49.9 | 66.6 |
| 14 | 29.5 | 69 | Sm 1.5 | 49.5 | 65.4 |
| 15 | 41.6 | 52.1 | Sm 6.3 | 64.3 | 78.8 |
| 16 | 50 | 41.7 | Sm 8.4 | 71.3 | 82.2 |
| 17 | 62.4 | 33.5 | Sm 4.1 | 72.8 | 82.2 |
| 18 | 62.5 | 19 | Sm 18.5 | 59.8 | 70.1 |
| 19 | 79.5 | 18.3 | Sm 2.2 | 43.2 | 73.1 |
| 20 | 25 | 63 | Gd 12 | 49.5 | 66.2 |
| 21 | 57 | 33 | Gd 10 | 60.1 | 72.2 |
| 22 | 25 | 63 | Dy 12 | 50.7 | 66.3 |
| 23 | 57 | 33 | Dy 10 | 59.8 | 71.5 |
| 24 | 47.5 | 33 | Mg 19.5 | 60.1 | 71.5 |
| 25 | 54 | 40 | Mg 6 | 65.2 | 77.3 |
| 26 | 54 | 40 | Ca 6 | 66.1 | 78.8 |
| 27 | 54.1 | 26.1 | Ca 19.8 | 60.1 | 72.2 |
| 28 | 56.2 | 30.1 | Ca 13.7 | 65.0 | 78.0 |
| 29 | 62 | 34 | Ca 4 | 73.8 | 82.3 |
| 30 | 62 | 33 | Sm 3 Ca 2 | 72.5 | 82.0 |
| 31 | 60 | 34 | La 2 Sm 2 Ca 2 | 73.3 | 82.2 |
| 32 | 61 | 33 | Y 1 La 1 Ce 1 Sm 1 Ca 1 Mg 1 | 71.2 | 81.0 |
| 33 | 60 | 34 | Nd 1 Sm 1 Gd 1 Dy 1 Ca 1 Mg 1 | 73.5 | 82.2 |

Example 3

Catalysts were prepared by adding $Sm(NO_3)_3 \cdot 6H_2O$ or $Ca(NO_3)_2$ and, $Ni(NO_3)_2$ together with one or two of $Co(NO_3)_2$ and $Fe(NO_3)_3$ to a mixtures of aqueous zirconia sol, and subsequent drying, calcination and reduction. The carbon dioxide conversion of the catalysts was examined by the same procedures as Example 1. The results are shown in Table 3. All the catalysts showed high conversion to methane at 200° and 250° C.

TABLE 3

| | Composition of Metallic Elements in the Catalysts Atomic % | | | | | Conversion of CO$_2$ % | |
|---|---|---|---|---|---|---|---|
| No. | Ni | Fe | Co | Zr | Sm | Ca | 200° C. | 250° C. |
| 34 | 30 | 20 | | 41.8 | 8.2 | | 49.7 | 63.1 |
| 35 | 30 | | 20 | 41.8 | 8.2 | | 53.5 | 65.4 |
| 36 | 30 | 10 | 10 | 41.8 | 8.2 | | 46.5 | 59.7 |
| 37 | 36 | 24 | | 36 | | 4 | 59.8 | 71 |
| 38 | 36 | | 24 | 36 | | 4 | 60.1 | 72.1 |
| 39 | 36 | 12 | 12 | 36 | | 4 | 58.0 | 70 |

Example 4

Catalyst were prepared as in Example 1 by adding Sm(NO$_3$)$_3$.6H$_2$O, Ca(NO$_3$)$_2$ or Ni(NO$_3$)$_2$ mixed in various ratios to aqueous zirconia sol, and subsequent drying, calcination and reduction. A reactant gas which consists of, in molar %, CO:15.5%, CO$_2$:14.5% and H$_2$:70% was passed through the reactor tube, in which the catalysts were kept at 300° C. Flow rate of the reactant gas is 5.4 L/Hr per catalyst 1.0 g (based on the precursors). The outlet of the reactor was led to a gas chromatography to analyze the reaction gas, and the conversion was determined from the ratio of the introduced gases and the unreacted gases.

The results are shown in Table 4. It was ascertained that all the catalysts, at 300° C., first converted whole the carbon monoxide to methane, and then, the remaining hydrogen was used for converting carbon dioxide to methane.

TABLE 4

| | Composition of Metallic Elements in the Catalysts Atomic % | | | | Conversion at 300° C. % | | |
|---|---|---|---|---|---|---|---|
| No. | Ni | Zr | Sm | Ca | CO | CO$_2$ | H$_2$ |
| 40 | 25 | 62.5 | 12.5 | | 100 | 26 | 88 |
| 41 | 30 | 58 | 12 | | 100 | 28 | 89.6 |
| 42 | 50 | 41.7 | 8.3 | | 100 | 28.5 | 90 |
| 43 | 70 | 25 | 5 | | 100 | 27 | 88.8 |
| 44 | 62 | 34 | | 4 | 100 | 28.5 | 90 |

We claim:

1. A process for methanation of carbon oxides, which comprises contacting a mixed gas of carbon dioxide, mixture of carbon dioxide and carbon dioxide, or a mixture containing at least one of them as main components and hydrogen with a catalyst consisting of, based on the metals in the elemental state:
    A) Zr for providing tetragonal zirconia supporter: 18-70 atomic %,
    B) one or more of tetragonal zirconia-stabilizing element selected from the group consisting of Y, La, Ce, Pr, Nd, Sm, Gd, Dy, Ca and Mg (in case of two or more are used, in total): 1-20 atomic %, and
    C) at least one of the iron group elements being supported on the tetragonal zirconia supporter and acting as the active site: 25-80 atomic %;
    wherein the stabilizing element or elements and a portion of the iron group element or elements are incorporated in the tetragonal zirconia supporter; and
    wherein the iron group element or elements not incorporated in the supporter are supported on the supporter in the metallic state.

2. The process of claim 1, wherein:
    the iron group element acting as the active site is Ni.

3. The process of claim 1, wherein:
    the iron group elements acting as the active site are Ni and one or both of Co and Fe, provided that Ni shares 0.6 or more based on the atomic ratio.

* * * * *